(12) United States Patent  (10) Patent No.:   US 6,372,920 B1
Minaskanian et al.          (45) Date of Patent:  Apr. 16, 2002

(54) PROCESS FOR PREPARING NITROGEN-SUBSTITUTED AMINOTETRALINS

(75) Inventors: Gevork Minaskanian, Richmond; Keith Rippel, Midlothian, both of VA (US)

(73) Assignee: Aderis Pharmaceuticals, Inc., Richmond, VA (US)

( * ) Notice: Subject to any disclaimer, the term of this patent is extended or adjusted under 35 U.S.C. 154(b) by 0 days.

(21) Appl. No.: 09/713,308

(22) Filed: Nov. 16, 2000

Related U.S. Application Data

(60) Provisional application No. 60/167,009, filed on Nov. 23, 1999.

(51) Int. Cl.$^7$ ............................................ C07D 333/20
(52) U.S. Cl. ............................................................ 549/75
(58) Field of Search ........................................... 549/75

(56) References Cited

U.S. PATENT DOCUMENTS

| | | | |
|---|---|---|---|
| 4,410,519 A | 10/1983 | Seiler et al. ................. | 424/226 |
| 4,564,628 A | 1/1986 | Horn .......................... | 514/438 |
| 4,968,837 A | 11/1990 | Manimaran et al. ........ | 562/470 |
| 5,382,596 A | 1/1995 | Sleevi et al. ................. | 514/459 |

OTHER PUBLICATIONS

Kanao, M., et al., "Spasmolytic Agents. 2. 1,2,3,4–Tetrahydro–2–naphthylamine Derivatives," *J. Med. Chem.* 25:1358–1363, American Chemical Society (1982).

Horn, A.S. et al., "Synthesis and radioreceptor binding activity of N–0437, a new, extremely potent and selective D$^2$ dopamine receptor agonist," *Pharmaceut. Weekblad Sci. Ed.* 7:208–211, Royal Dutch Association for Advancement of Pharmacy (1985).

McDermed, J., et al., "Synthesis and Dopaminergic Activity of (±)–, (+)–, and (–)–2–Dipropylamino–5–hydoxy–1,2,3,4–tetrahydronaphthalene," *J. Med. Chem.* 19:547–549, American Chemical Society (1976).

*Primary Examiner*—Amelia Owens
(74) *Attorney, Agent, or Firm*—Sterne, Kessler, Goldstein & Fox PLLC

(57) ABSTRACT

The present invention relates to a process for preparing optically active and racemic nitrogen-substituted 2-aminotetralins of the following Formula (I):

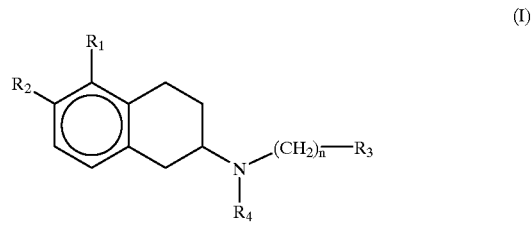

(I)

wherein $R_1$, $R_2$, $R_3$, $R_4$, and n are set in the specification, wherein the process comprises alkylating the corresponding unsubstituted 2-aminotetralin of Formula (II):

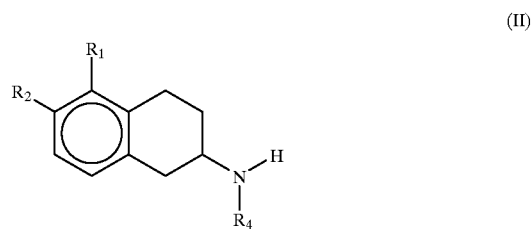

(II)

with a reactant of the Formula (III):

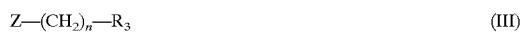

$Z$—$(CH_2)_n$—$R_3$  (III)

wherein Z is a leaving group, in the presence of a base, wherein the base is selected from the group consisting of alkali metal carbonate and alkali metal bicarbonate, and wherein the amount of the base is less than about a 1.9-fold molar excess with respect to the amount of the 2-aminotetralin.

16 Claims, No Drawings

PROCESS FOR PREPARING NITROGEN-SUBSTITUTED AMINOTETRALINS

This application claims benefit of provisional application No. 60/167,009, filed Nov. 23, 1999.

BACKGROUND OF THE INVENTION

1. Field of the Invention

The present invention relates to a process for preparing nitrogen-substituted aminotetralins. Particularly, the invention relates to the alkylation of 2-aminotetralins wherein the alkylation is performed in the presence of a base selected from the group consisting of alkali metal carbonate or alkali metal bicarbonate, and wherein the amount of the base is less than about a 1.9-fold molar excess with respect to the starting material.

2. Related Art

A variety of conventional synthetic methods have been used to prepare nitrogen-substituted 2-aminotetralins included in the following Formula (I):

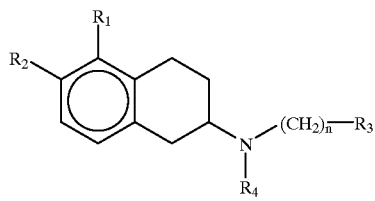

(I)

wherein $R_1$ is OA; $R_2$ is selected from the group consisting of H and OA; A is H or is selected from the group consisting of hydrocarbyl radicals comprising between 1 and 3 carbon atoms, as well as one of the following radicals

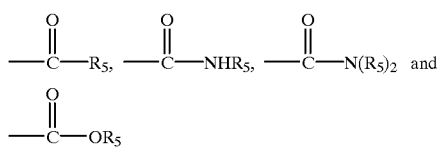

wherein $R_5$ is selected from the group consisting of alkyl and aromatic residues having from 1 to 20 carbon atoms; $R_3$ is selected from the group consisting of alkoxy, cycloalkoxy, optionally substituted phenyl, 3-pyridyl, 4-pyridyl,

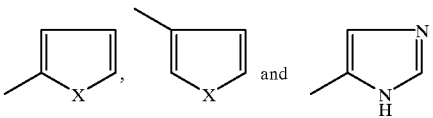

where X is S, O or NH; $R_4$ is an unbranched alkyl chain having from 1 to 3 carbon atoms; and n is an integer from 1 to 5.

For example, Horn, A. S., et al., *Pharmaceutisch Weekblad Sci. Ed.* 7:208–211 (1985) describes a reductive amination wherein 2-(N-n-propylamino)-5-methoxytetralin and 2-thiopheneacetic acid are reacted in the presence of trimethylaminoborohydride to produce 2-(N-n-propyl-N-2-thienylethylamino)-5-methoxytetralin. The product is further reacted with a solution of $BBr_3$ to produce 2-(N-n-propyl-N-2-thienylethylamino)-5-hydroxytetralin. The reaction scheme can be presented as follows, wherein n is 2, $R_4$ is n-propyl and $R_3$ is thienyl:

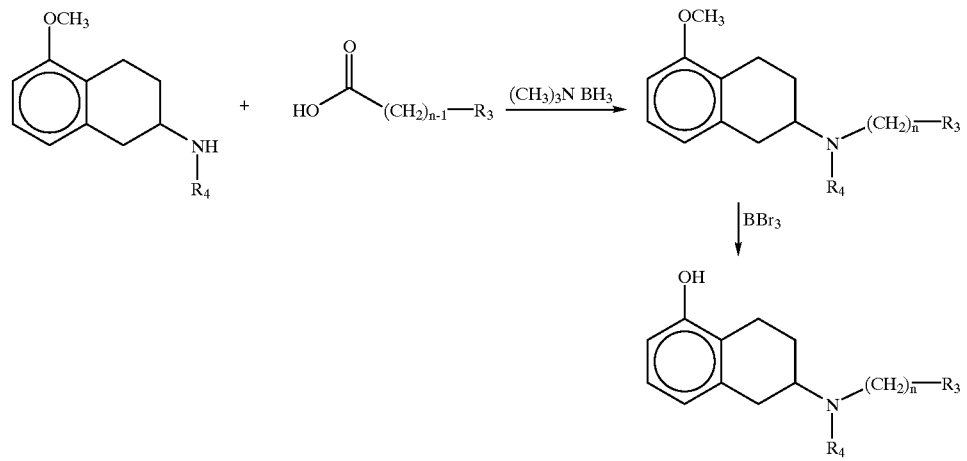

U.S. Pat. No. 5,382,596 describes an alkylation reaction of the following scheme wherein $R_4$ is an unbranched alkyl chain comprising from 1 to 3 carbon atoms or a cyclopropylmethyl radical and $R_6$ is $—(CH_2)_n—R_3$, wherein n is an integer from 1 to 4 and $R_3$ is alkoxy, cycloalkoxy or a cyclic ether:

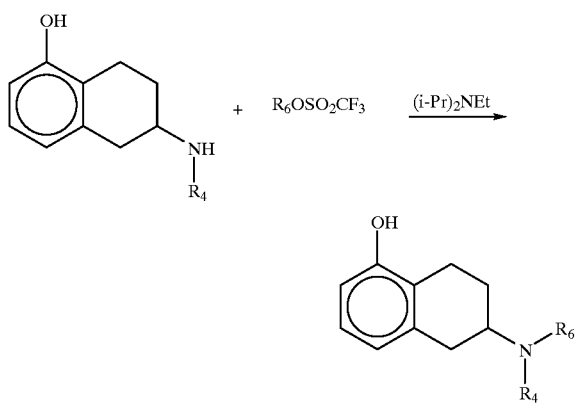

U.S. Pat. No. 4,410,519 describes the following alkylation reaction, wherein $R_4$ is alkyl of 1 to 4 carbon atoms, A is $-(CH_2)_n-$, wherein n is 1 to 5 and Z is a leaving group, preferably chlorine, bromine, iodine, alkylsulfonyloxy or arylsulfonyloxy:

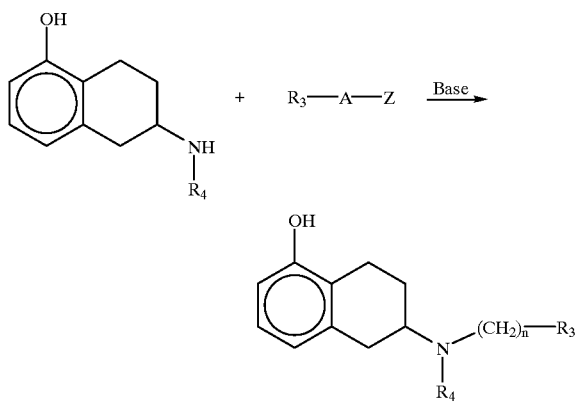

In the above reaction, the presence of the base is optional and it may be, e.g., a tertiary amine or an alkali metal carbonate or bicarbonate.

Conventional alkylation reactions produce acidic by-products from the leaving groups within the alkylating agents employed. If these acidic by-products are not neutralized, the progress of the reaction is frequently harmed either by: (a) the starting material, i.e., the amine, serving as an acid scavenger and precipitating from solution, thereby terminating the reaction, or (b) the acidic by-products degrading the starting material and/or alkylating agent, thereby terminating the reaction or producing increased amounts of impurities. In order to avoid these problems, such alkylations typically employ a large excess of base, commonly greater than two-fold molar excess with respect to the starting material.

The conventional alkylation methods described above suffer from limited product yields resulting from incomplete reactions and inefficient purification procedures required to reduce the levels of impurities. Nitrogen-substituted 2-aminotetralins are useful as pharmaceutical agents that treat a number of diseases and, therefore, product purity is a major concern. Attempts are being made to improve yields and to efficiently produce more pure products. Manufacturing problems are particularly acute when very expensive chiral starting materials are used. It can be readily seen that even minor improvements in process efficiency will result in economic benefits. This is particularly true upon scaleup manufacture of chirally pure products. A need therefore exists for processes of synthesis having improved yields, shorter reaction times and purer products.

SUMMARY OF THE INVENTION

Alkali metal carbonates and alkali metal bicarbonates are used as acid scavengers in alkylation reactions that attach substituents on the nitrogen atom in 2-aminotetralins. It has now been discovered that the amount of alkali metal carbonate or alkali metal bicarbonate used in these alkylation reactions is a critically important factor in the course of the reaction. Applicants found that the amount of alkali metal carbonate or alkali metal bicarbonate should be less than about a 1.9-fold molar excess with respect to the 2-aminotetralin starting material.

It has been discovered that the use of limited amounts of alkali metal carbonate or alkali metal bicarbonate in these reactions gives a more efficient process for preparing N-substituted 2-aminotetralins than the prior art processes used for preparing these compounds, allowing the production of more pure products and, thus, avoiding extensive purification procedures. Accordingly, the present invention provides a process for preparing 2-aminotetralins of the Formula (I):

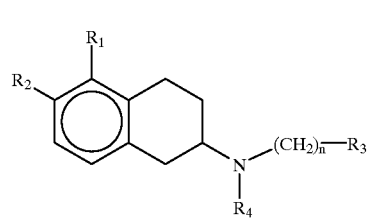

wherein $R_1$ is OA; $R_2$ is selected from the group consisting of H and OA; A is H or is selected from the group consisting of a straight or a branched alkyl chain having from 1 to 3 carbon atoms,

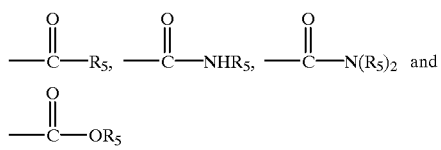

wherein $R_5$ is selected from the group consisting of $C_1-C_{20}$ alkyl, $C_6-C_{10}$ aryl and $C_7-C_{20}$ arylalkyl; $R_3$ is selected from the group consisting of alkoxy, cycloalkoxy, optionally substituted phenyl, 3-pyridyl, 4-pyridyl,

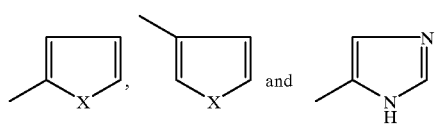

where X is S, O or NH; $R_4$ is an unbranched alkyl chain having from 1 to 3 carbon atoms; and n is an integer from 1 to 5.

The process comprises allowing a 2-aminotetralin of Formula (II):

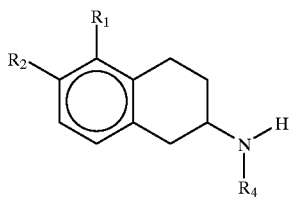

(II)

wherein $R_1$, $R_2$ and $R_4$ are as defined above, to react with a reactant of Formula (III):

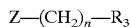

(III)

wherein $R_3$ and n are as defined above and Z is a leaving group, in the presence of a base, wherein the base is selected from the group consisting of alkali metal carbonate and alkali metal bicarbonate, and wherein the amount of the base is less than about a 1.9-fold molar excess with respect to the amount of the 2-aminotetralin.

Preferably, from about 0.2 to about 1.8 mole ratio, more preferably from about 0.2 to about 1.5 mole ratio, more preferably from about 0.3 to about 1.3 mole ratio of alkali metal carbonate or alkali metal bicarbonate with respect to the 2-aminotetralin starting material is used. Especially, from about 0.3 to about 1.0 mole ratio, more especially from about 0.4 to 0.8 mole ratio, specifically from about 0.4 to about 0.7 mole ratio, of alkali metal carbonate or alkali metal bicarbonate with respect to the 2-aminotetralin starting material is used as an acid scavenger.

Further, the present invention provides an improvement in a method of alkylating 2-aminotetralin of Formula (II), wherein $R_1$, $R_2$ and $R_4$ are as defined above, with a reactant of Formula (III), wherein $R_3$ and n are as defined above and Z is a leaving group, in the presence of a base, the improvement comprising employing a base selected from the group consisting of alkali metal carbonate and alkali metal bicarbonate, wherein the amount of the base is less than about a 1.9-fold molar excess with respect to the amount of the 2-aminotetralin.

Additional embodiments and advantages of the invention will be set forth in part in the description as follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE PREFERRED EMBODIMENTS

Applicants found that by reducing the amount of base in a process for preparing nitrogen-substituted 2-aminotetralins of Formula (I) the amount of by-products was essentially decreased and, thus, more pure products were achieved. It was discovered that less than about a 1.9-fold molar excess of an alkali metal carbonate or an alkali metal bicarbonate with respect to the amine starting material is an ideal amount to be used as an acid scavenger. The products of Formula (I) can be optically active or racemic.

The reaction scheme of the process according to the invention can be presented as follows:

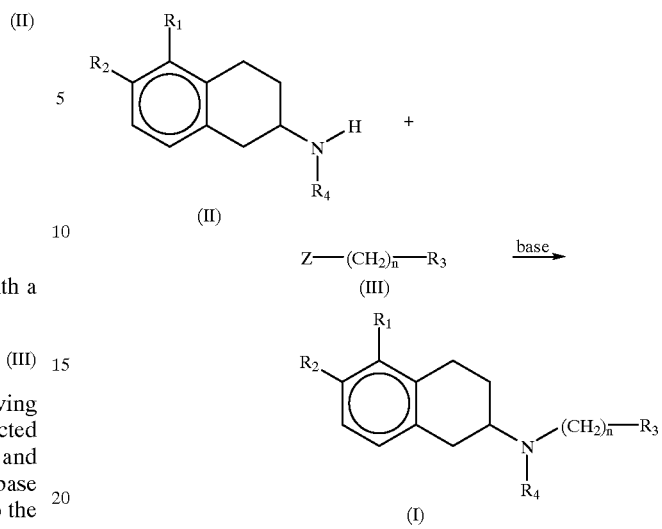

In the above formulae, $R_1$ is OA; $R_2$ is selected from the group consisting of H and OA; A is H or is selected from the group consisting of a straight or a branched alkyl chain having from 1 to 3 carbon atoms,

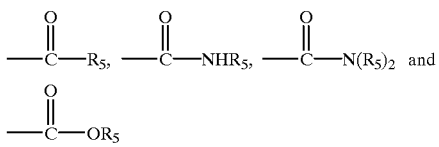

wherein R5 is selected from the group consisting of $C_1$–$C_{20}$ alkyl, $C_6$–$C_{10}$ aryl and $C_7$–$C_{20}$arylalkyl; $R_3$ is selected from the group consisting of alkoxy, cycloalkoxy, optionally substituted phenyl, 3-pyridyl, 4-pyridyl,

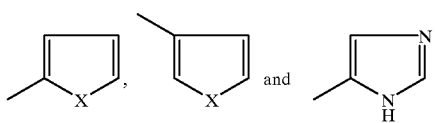

where X is S, O or NH; R4 is an unbranched alkyl chain having from 1 to 3 carbon atoms; n is an integer from 1 to 5; and Z is a leaving group.

A is preferably H, $CH_3$ or —C(O)—$R_5$, most preferably hydrogen.

Preferably $R_5$ is selected from the group of $C_1$–$C_{12}$ alkyl, $C_6$–$C_{10}$ aryl and $C_7$–$C_{12}$arylalkyl, such as phenyl, methyl, tertiary butyl, methylphenyl, o-, m-, or p-methoxyphenyl.

Preferably, $R_3$ is selected from the group consisting of phenyl, hydroxyphenyl, thienyl, especially 2-thienyl and 3-thienyl, and alkoxy. Preferably, alkoxy is selected from the group consisting of ethoxy, propoxy, isopropoxy, butoxy, secondary butoxy, isobutoxy, and tertiary butoxy.

In the more preferred compounds, $R_2$ is H and n is an integer from 1 to 3.

Z is preferably chlorine, bromine, iodine, alkylsulfonyloxy, such as trifluoromethylsulfonyloxy, or arylsulfonyloxy, such as benzenesulfonyloxy or toluenesulfonyloxy.

Alkyl means straight or branched hydrocarbon alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl, and eicosyl.

Alkoxy means straight-chain or branched alkoxy having 1 to 5 carbon atoms and includes, for example, methoxy, ethoxy, propoxy, isopropoxy, butoxy, iso-butoxy, secondary butoxy, tertiary butoxy, pentyloxy, and isopentyloxy.

Cycloalkoxy means a cycloalkyl group with a single covalent bond to an oxygen atom where the cycloalkyl moiety is a cyclic alkyl group having 3 to 6 carbon atoms.

Aryl means phenyl or naphthyl or substituted phenyl or substituted naphthyl which are phenyl or naphthyl substituted by at least one substituent selected from the group consisting of halogen (chlorine, bromine, fluorine, or iodine), amino, nitro, hydroxy, and alkyl.

A preferred compound produced by the process according to the invention is (−)-5-hydroxy-2-[N-n-propyl-N-2-(2-thienyl)ethylamino]tetralin.

Preferably, from about 0.2 to about 1.8 mole ratio, more preferably from about 0.2 to about 1.5 mole ratio, more preferably from about 0.3 to about 1.3 mole ratio of alkali metal carbonate or alkali metal bicarbonate with respect to the 2-aminotetralin starting material is used. Especially, from about 0.3 to about 1.0 mole ratio, more especially from about 0.4 to 0.8 mole ratio, specifically from about 0.4 to about 0.7 mole ratio, of alkali metal carbonate or alkali metal bicarbonate with respect to the 2-aminotetralin starting material is used as an acid scavenger.

Preferably, the alkali metal carbonate is sodium carbonate and the alkali metal bicarbonate is sodium bicarbonate. Other useful bases include potassium carbonate and potassium bicarbonate.

Preferably, the reactant is Z—(CH$_2$)$_n$—R$_3$, wherein Z, n and R$_3$ are as defined above. Useful reactants include 2-(2-thienyl)ethanol benzenesulfonate and 2-(2-thienyl) ethanol toluenesulfonate.

The decreased amounts of alkali metal carbonate or alkali metal bicarbonate in the process according to the invention allow the production of more pure products without the requirement of extensive purification procedures. Further, this way of minimizing the production of by-products allows the addition of additional alkylating reactant in order to accelerate the completion of the reaction without incurring an unacceptably complex product mixture. The resultant savings in reaction time constitutes a significant advantage when costly large scale manufacturing equipment is employed.

Table 1 below shows clearly that the conventionally-used large excess of alkali metal carbonate or bicarbonate, i.e., greater than a two-fold molar excess with respect to the starting material, results in reaction mixtures containing undesirable amounts of impurities that complicate attempts at product isolation. Further, the reaction time is substantially longer when a large excess of the base is used.

The process of the invention may be conveniently effected at temperatures from about 90° C. to about 180° C., preferably from about 110° C. to about 145° C.

The starting materials, e.g., the compounds of Formula (II) and (III), are either known or may be produced in known manner or analogous to the methods described herein. For example, the 2-aminotetralin starting materials can be prepared as described in U.S. Pat. Nos. 4,968,837 and 4,564, 628. Optically active compounds may be produced from optically active starting materials.

The invention will be further clarified by the following examples, which are intended to be purely exemplary of the invention.

EXAMPLE 1

700 mg (3.4 mmol) (−)-5-hydroxy-N-n-propyl-2-aminotetralin made by the process described in U.S. Pat. No. 5,382,596, 4.8 g (17 mmol) 2-(2-thienyl)ethanol toluenesulfonate, 216 mg (2 mmol) sodium carbonate (0.6 molar ratio Na$_2$CO$_3$/amine starting material), and 40 mL xylenes (mixture, Aldrich Chemical Co.) were mixed and brought to reflux. The reaction was halted at 24 hours, and worked up in the usual manner well known to those skilled in the art without chromatographic purification to yield the product, (−)-5-hydroxy-2-[N-n-propyl-N-2-(2-thienyl) ethylamino]tetralin, that was converted to its hydrochloride salt form, with a yield of 1 g (84%).

EXAMPLE 2

13.1 kg (63.9 mol) (−)-5-hydroxy-N-n-propyl-2-aminotetralin, 51.6 kg (182 mol) 2-(2-thienyl)ethanol toluenesulfonate, and 4.1 kg (38.6 mol) sodium carbonate (0.6 molar ratio Na$_2$CO$_3$/amine starting material) were mixed in a reactor under a nitrogen atmosphere using xylenes (150 kg) as a solvent with vigorous agitation and heated to a temperature of 120° C. to 125° C. for a period of 32 hours. HPLC analysis of the reaction mixture showed less than 2% of the starting material remaining, and the reaction was halted. The product, (−)-5-hydroxy-2-[N-n-propyl-N-2-(2-thienyl)ethylamino]tetralin, was isolated in the usual manner well known to those skilled in the art without chromatographic purification to yield product that was converted to its hydrochloride salt form, with a yield of 13.2 kg (59%).

EXAMPLE 3

600 mg (3.0 mmol) (−)-5-hydroxy-N-n-propyl-2-aminotetralin, 1.2 g (4.0 mmol) 2-(2-thienyl)ethanol toluenesulfonate, 3 g (28.3 mmol) sodium carbonate (9.4 molar ratio Na$_2$CO$_3$/amine starting material), and 35 mL xylenes were mixed and brought to reflux. The reaction was incomplete at 24 hours and was continued for 48 hours. Analysis of the product mixture showed a majority of side products, and isolation of the desired product, (−)-5-hydroxy-2-[N-n-propyl--N-2-(2-thienyl)ethylamino] tetralin, was abandoned due to the poor yield.

EXAMPLE 4

388 g (1.89 mol) (−)-5-hydroxy-N-n-propyl--aminotetralin, 582 g (2.17 mol) 2-(2-thienyl)ethanol benzenesulfonate, 622 g (5.86 mol) sodium carbonate (3.1 molar ratio Na$_2$CO$_3$/amine starting material), and 4 L xylenes (mixture of xylenes) were mixed in a reactor under a nitrogen atmosphere with vigorous agitation and heated to reflux for a period of 48 hours. The reaction was halted, and crude product was isolated in the usual manner. The crude product was dissolved in a minimal amount of ethyl acetate/ hexane (1:1) and loaded on a silica gel chromatographic column. The mixture was eluted initially with 40 L ethyl acetate/hexane (1:19) to allow lipophilic impurities to pass through the column (monitored by thin layer chromatography). The column was then eluted with 30 L ethyl acetate/hexane (1:9) to elute the desired product, (−)-5-hydroxy-2-[N-n-propyl-N-2-(2-thienyl)ethylamino] tetralin, with thin layer chromatography analysis of fractions used to determine which fractions to combine. The combined fractions were then concentrated and the residue converted to its hydrochloride salt form in the usual manner, with a yield of 367 g (55%).

Table 1 below summarizes the results of Examples 1 to 4. The results of Examples 1 and 2 show that the use of less than about a 1.9-fold molar excess of alkali metal carbonate or alkali metal bicarbonate with respect to the 2-aminotetralin starting material results in an unexpectedly pure product and, thus, extensive purification procedures are avoided. These findings were demonstrated over a large range of reaction scales. Further, the use of decreased amounts of alkali metal carbonate or alkali metal bicarbonate decreases the reaction times.

Examples 3 and 4 demonstrate that the conventionally-used excess of alkali metal carbonate or bicarbonate used as an acid scavenger in alkylation reactions produces impure mixtures requiring laborious purification procedures for isolating the product.

TABLE 1

Comparison of the Results of Examples 1 to 4.

| Example | Molar Ratio of $Na_2CO_3$ Used* | Scale of Reaction/grams of amine starting material | Reaction Time/h | Extensive Purification (Chromatography) of Product Required |
|---|---|---|---|---|
| 1 | 0.6 | 0.7 | 24 | No |
| 2 | 0.6 | 13,100 | 32 | No |
| 3 | 9.4 | 0.6 | 48 | Yes |
| 4 | 3.1 | 388 | 48 | Yes |

*Ratio of $Na_2CO_3$ to 2-aminotetralin starting material.

Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All publications, patent applications and patents cited herein are fully incorporated by reference.

What is claimed is:

1. A process for preparing an optically active or a racemic compound of the following general formula:

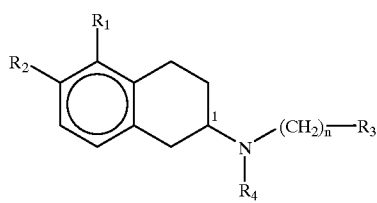

wherein $R_1$ is OA; $R_2$ is selected from the group consisting of H and OA; wherein A is H or is selected from, the group consisting of a straight or a branched alkyl chain having from 1 to 3 carbon atoms,

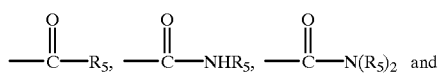

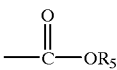

wherein $R_5$ is selected from the group consisting of $C_1$–$C_{20}$ alkyl, $C_6$–$C_{10}$ aryl and $C_7$–$C_{20}$ arylalkyl; $R_3$ is selected from the group consisting of alkoxy, cycloalkoxy, optionally substituted phenyl, 3-pyridyl, 4-pyridyl,

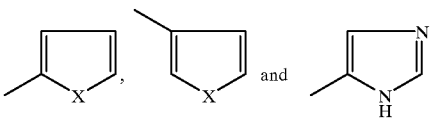

wherein X is O, S or NH; $R_4$ is an unbranched alkyl chain having from 1 to 3 carbon atoms; and n is an integer from 1 to 5, wherein the process comprises allowing a 2-aminotetralin of the formula:

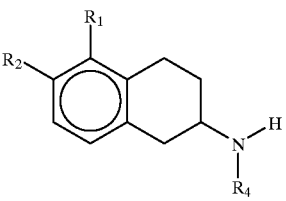

to react with a reactant of the formula:

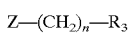

wherein $R_3$ and n are as defined above, and Z is a leaving group, in the presence of a base, wherein the base is selected from the group consisting of alkali metal carbonate and alkali metal bicarbonate, and wherein the amount of the base is less than about a 1.9-fold molar excess with respect to the amount the 2-aminotetralin.

2. The process according to claim 1, wherein the amount of the base is from about 0.2 to about 1.8 mole ratio with respect to the 2-aminotetralin.

3. The process according to claim 2, wherein the amount of the base is from about 0.2 to about 1.5 mole ratio with respect to the 2-aminotetralin.

4. The process according to claim 3, wherein the amount of the base is from about 0.3 to about 1.3 mole ratio with respect to the amount of the 2-aminotetralin.

5. The process according to claim 4, wherein the amount of the base is from about 0.3 to about 1 mole ratio with respect to the 2-aminotetralin.

6. The process according to claim 5, wherein the amount of the base is from about 0.4 to about 0.8 mole ratio with respect to the 2-aminotetralin.

7. The process according to claim 6, wherein the amount of the base is from about 0.4 to about 0.7 mole ratio with respect to the amount of the 2-aminotetralin.

8. The process according to claim 7, wherein the amount of the base is about 0.6 mole ratio with respect to the 2-aminotetralin.

9. The process according to claim 1, wherein the alkali metal carbonate is sodium carbonate.

10. The process according to claim 1, wherein the alkali metal bicarbonate is sodium bicarbonate.

11. The process according to claim 1, wherein $R_3$ is selected from the group consisting of alkoxy, phenyl and thienyl.

12. The process according to claim 11, wherein the alkoxy is selected from the group consisting of ethoxy, propoxy, isopropoxy, butoxy, secondary butoxy, isobutoxy, and tertiary butoxy.

13. The process according to claim 1, wherein the reactant is 2-(2-thienyl)ethanol benzenesulfonate or 2-(2-thienyl)ethanol toluenesulfonate.

14. The process according to claim 1, wherein A is H and $R_2$ is H.

15. The process according to claim 1, wherein the 2-aminotetralin starting material is (−)-5-hydroxy-2-N-propylaminotetralin.

16. The process according to claim 1, wherein the product prepared is (−)-5-hydroxy-2-[N-n-propyl-N-2-(2-thienyl)ethylamino]tetralin.

* * * * *